(12) United States Patent
Long

(10) Patent No.: US 8,480,750 B2
(45) Date of Patent: Jul. 9, 2013

(54) MODULAR GLENOID PROSTHESIS

(75) Inventor: Jack F Long, Warsaw, IN (US)

(73) Assignee: Depuy Synthes Products, LLC, Raynham, MA (US)

( * ) Notice: Subject to any disclaimer, the term of this patent is extended or adjusted under 35 U.S.C. 154(b) by 132 days.

(21) Appl. No.: 12/953,522

(22) Filed: Nov. 24, 2010

(65) Prior Publication Data

US 2012/0130499 A1    May 24, 2012

(51) Int. Cl.
*A61F 2/40* (2006.01)
(52) U.S. Cl.
USPC ............................................ 623/19.11
(58) Field of Classification Search
CPC ................................................ A61F 2/40
USPC .................................. 623/19.11–19.14
IPC .................................................. A61F 2/40
See application file for complete search history.

(56) References Cited

U.S. PATENT DOCUMENTS

| | | | |
|---|---|---|---|
| 3,061,977 A | 11/1962 | Schmidt |
| 3,694,820 A | 10/1972 | Scales |
| 3,837,008 A | 9/1974 | Bahler |
| 3,855,638 A | 12/1974 | Pilliar |
| 4,040,130 A | 8/1977 | Laure |
| 4,042,980 A | 8/1977 | Swanson |
| 4,045,825 A | 9/1977 | Stroot |
| 4,045,826 A | 9/1977 | Stroot |
| 4,106,128 A | 8/1978 | Greenwald |
| 4,172,296 A | 10/1979 | D'Errico |
| 4,180,871 A | 1/1980 | Hamas |
| 4,524,467 A | 6/1985 | DeCarlo, Jr. |
| 4,550,450 A | 11/1985 | Kinnett |
| D285,968 S | 9/1986 | Kinnett |
| 4,693,723 A | 9/1987 | Gabard |
| 4,695,282 A | 9/1987 | Forte |
| 4,795,468 A | 1/1989 | Hodorek |
| 4,865,025 A | 9/1989 | Buzzi |
| 4,865,605 A | 9/1989 | Dines |
| 4,919,670 A | 4/1990 | Dale |
| 4,936,853 A | 6/1990 | Fabian |
| 4,964,865 A | 10/1990 | Burkhead |
| 4,986,833 A | 1/1991 | Worland |
| 4,987,904 A | 1/1991 | Wilson |

(Continued)

FOREIGN PATENT DOCUMENTS

| | | |
|---|---|---|
| DE | 102006041550 | 11/2007 |
| DE | 102008021110 A1 | 10/2009 |

(Continued)

OTHER PUBLICATIONS

Translation of FR2652498A1—Inventor: Michael Columbier, Date of Publ. Oct. 4, 1989.

(Continued)

*Primary Examiner* — Thomas J Sweet
*Assistant Examiner* — Jason-Dennis Stewart

(57) ABSTRACT

A modular glenoid assembly. The modular glenoid assembly includes a base having a first side and an opposing second side, the first side including a plurality of connection features arranged in an array. At least one glenoid attachment member is included. The glenoid attachment member has a locking mechanism sized and shaped to lock the glenoid attachment member in at least one of the plurality of connection features on the base.

13 Claims, 7 Drawing Sheets

U.S. PATENT DOCUMENTS

| | | | |
|---|---|---|---|
| 5,030,219 | A | 7/1991 | Matsen, III |
| 5,032,132 | A | 7/1991 | Matsen, III |
| 5,047,058 | A | 9/1991 | Roberts |
| 5,080,673 | A | 1/1992 | Burkhead |
| 5,108,446 | A | 4/1992 | Wagner |
| 5,150,304 | A | 9/1992 | Berchem |
| 5,197,465 | A | 3/1993 | Montgomery |
| 5,201,882 | A | 4/1993 | Paxson |
| 5,304,181 | A | 4/1994 | Caspari |
| 5,314,479 | A | 5/1994 | Rockwood, Jr. |
| 5,344,461 | A | 9/1994 | Phlipot |
| 5,358,526 | A | 10/1994 | Tornier |
| 5,370,693 | A | 12/1994 | Kelman |
| 5,387,241 | A | 2/1995 | Hayes |
| 5,437,677 | A | 8/1995 | Shearer |
| 5,458,637 | A | 10/1995 | Hayes |
| 5,474,559 | A | 12/1995 | Bertin |
| 5,486,180 | A | 1/1996 | Dietz |
| 5,489,309 | A | 2/1996 | Lackey |
| 5,489,310 | A | 2/1996 | Mikhail |
| 5,496,324 | A | 3/1996 | Barnes |
| 5,507,821 | A | 4/1996 | Sennwald |
| 5,554,158 | A | 9/1996 | Vinciguerra |
| 5,593,441 | A | 1/1997 | Lichtenstein |
| 5,593,448 | A | 1/1997 | Dong |
| 5,601,563 | A | 2/1997 | Burke |
| 5,665,090 | A | 9/1997 | Rockwood |
| 5,702,447 | A | 12/1997 | Walch |
| 5,718,360 | A | 2/1998 | Green |
| 5,723,018 | A | 3/1998 | Cyprien |
| 5,743,915 | A | 4/1998 | Bertin |
| 5,769,855 | A | 6/1998 | Bertin |
| 5,779,710 | A | 7/1998 | Matsen, III |
| 5,782,924 | A | 7/1998 | Johnson |
| 5,800,551 | A | 9/1998 | Williamson |
| 5,853,415 | A | 12/1998 | Bertin |
| 5,860,981 | A | 1/1999 | Bertin |
| 5,879,401 | A | 3/1999 | Besemer |
| 5,908,424 | A | 6/1999 | Bertin |
| 5,928,285 | A | 7/1999 | Bigliani |
| 5,976,145 | A | 11/1999 | Kennefick, III |
| 6,045,582 | A | 4/2000 | Prybyla |
| 6,096,084 | A | 8/2000 | Townley |
| 6,139,581 | A | 10/2000 | Engh |
| 6,197,062 | B1 | 3/2001 | Fenlin |
| 6,197,063 | B1 | 3/2001 | Dews |
| 6,206,925 | B1 | 3/2001 | Tornier |
| 6,228,119 | B1 | 5/2001 | Ondrla |
| 6,228,900 | B1 | 5/2001 | Shen |
| 6,245,074 | B1 | 6/2001 | Allard |
| 6,281,264 | B1 | 8/2001 | Salovey |
| 6,364,910 | B1 | 4/2002 | Shultz |
| 6,368,353 | B1 | 4/2002 | Arcand |
| 6,379,386 | B1 | 4/2002 | Resch |
| 6,406,495 | B1 | 6/2002 | Schoch |
| 6,488,715 | B1 | 12/2002 | Pope |
| 6,514,287 | B2 | 2/2003 | Ondrla |
| 6,620,197 | B2 | 9/2003 | Maroney |
| 6,673,115 | B2 | 1/2004 | Resch |
| 6,676,705 | B1 | 1/2004 | Wolf |
| 6,679,916 | B1 | 1/2004 | Frankle |
| 6,699,289 | B2 | 3/2004 | Iannotti |
| 6,699,290 | B1 | 3/2004 | Wack et al. |
| 6,783,549 | B1 | 8/2004 | Stone |
| 6,875,234 | B2 | 4/2005 | Lipman |
| 6,893,702 | B2 | 5/2005 | Takahashi |
| 6,896,702 | B2 | 5/2005 | Collazo |
| 6,899,736 | B1 | 5/2005 | Rauscher |
| 6,911,047 | B2 | 6/2005 | Rockwood, Jr. |
| 6,942,699 | B2 | 9/2005 | Stone |
| 6,953,478 | B2 | 10/2005 | Bouttens |
| 7,033,396 | B2 | 4/2006 | Tornier |
| 7,051,451 | B2 | 5/2006 | Augostino |
| 7,090,677 | B2 | 8/2006 | Fallin |
| 7,160,328 | B2 | 1/2007 | Rockwood, Jr. |
| 7,160,331 | B2 | 1/2007 | Cooney, III |
| 7,169,184 | B2 | 1/2007 | Dalla Pria |
| 7,175,665 | B2 | 2/2007 | German |
| 7,204,854 | B2 | 4/2007 | Guederian |
| 7,329,284 | B2 | 2/2008 | Maroney |
| 7,527,631 | B2 | 5/2009 | Maroney |
| 7,604,665 | B2 | 10/2009 | Iannotti |
| 7,608,109 | B2 | 10/2009 | Dalla Pria |
| 7,621,961 | B2 | 11/2009 | Stone |
| 7,625,408 | B2 | 12/2009 | Gupta |
| 7,753,959 | B2 | 7/2010 | Berelsman |
| 7,766,969 | B2 | 8/2010 | Justin |
| 7,892,287 | B2 | 2/2011 | Deffenbaugh |
| 7,918,895 | B2 | 4/2011 | Isch |
| 7,922,769 | B2 | 4/2011 | Deffenbaugh |
| 7,927,335 | B2 | 4/2011 | Deffenbaugh |
| 2001/0011192 | A1 | 8/2001 | Ondrla |
| 2001/0018589 | A1 | 8/2001 | Muller |
| 2001/0037153 | A1 | 11/2001 | Rockwood |
| 2002/0004685 | A1 | 1/2002 | White |
| 2002/0082702 | A1 | 6/2002 | Resch |
| 2002/0095214 | A1 | 7/2002 | Hyde |
| 2002/0099445 | A1 | 7/2002 | Maroney |
| 2003/0028253 | A1 | 2/2003 | Stone |
| 2003/0045883 | A1 | 3/2003 | Chow |
| 2003/0055507 | A1 | 3/2003 | McDevitt |
| 2003/0065397 | A1 | 4/2003 | Hanssen |
| 2003/0097183 | A1 | 5/2003 | Rauscher |
| 2003/0114933 | A1 | 6/2003 | Bouttens |
| 2003/0125809 | A1 | 7/2003 | Iannotti |
| 2003/0149485 | A1 | 8/2003 | Tornier |
| 2003/0187514 | A1 | 10/2003 | McMinn |
| 2004/0064189 | A1 | 4/2004 | Maroney |
| 2004/0122519 | A1 | 6/2004 | Wiley |
| 2004/0122520 | A1 | 6/2004 | Lipman |
| 2004/0162619 | A1 | 8/2004 | Blaylock |
| 2004/0193277 | A1 | 9/2004 | Long |
| 2004/0193278 | A1 | 9/2004 | Maroney |
| 2004/0220673 | A1 | 11/2004 | Pria |
| 2004/0220674 | A1 | 11/2004 | Pria |
| 2004/0230312 | A1 | 11/2004 | Hanson |
| 2004/0236424 | A1 | 11/2004 | Berez |
| 2005/0021148 | A1 | 1/2005 | Gibbs |
| 2005/0049709 | A1 | 3/2005 | Tornier |
| 2005/0125068 | A1 | 6/2005 | Hozack |
| 2005/0171613 | A1 | 8/2005 | Sartorius |
| 2005/0261775 | A1 | 11/2005 | Baum |
| 2006/0030946 | A1 | 2/2006 | Ball |
| 2006/0069443 | A1 | 3/2006 | Deffenbaugh |
| 2006/0069444 | A1 | 3/2006 | Deffenbaugh |
| 2006/0074353 | A1 | 4/2006 | Deffenbaugh |
| 2006/0074430 | A1 | 4/2006 | Deffenbaugh |
| 2006/0079963 | A1 | 4/2006 | Hansen |
| 2006/0100498 | A1 | 5/2006 | Boyce |
| 2006/0100714 | A1 | 5/2006 | Ensign |
| 2006/0111787 | A1 | 5/2006 | Bailie |
| 2006/0149387 | A1 | 7/2006 | Smith |
| 2006/0149388 | A1 | 7/2006 | Smith |
| 2006/0161260 | A1 | 7/2006 | Thomas |
| 2006/0265079 | A1 | 11/2006 | D'Alessio |
| 2007/0055380 | A1 | 3/2007 | Berelsman |
| 2007/0142917 | A1 | 6/2007 | Roche |
| 2007/0179624 | A1 | 8/2007 | Stone |
| 2007/0219637 | A1 | 9/2007 | Berelsman |
| 2007/0219638 | A1 | 9/2007 | Jones |
| 2007/0225817 | A1 | 9/2007 | Reubelt |
| 2008/0046091 | A1 | 2/2008 | Weiss |
| 2008/0140209 | A1 | 6/2008 | Iannotti |
| 2008/0208348 | A1 | 8/2008 | Fitz |
| 2008/0234820 | A1 | 9/2008 | Felt |
| 2009/0125113 | A1 | 5/2009 | Guederian |
| 2009/0143865 | A1 | 6/2009 | Hassler |
| 2009/0204225 | A1 | 8/2009 | Meridew |
| 2009/0281630 | A1 | 11/2009 | Delince |
| 2009/0292364 | A1 | 11/2009 | Linares |
| 2009/0312839 | A1 | 12/2009 | Scheker |
| 2010/0030339 | A1 | 2/2010 | Berelsman et al. |
| 2010/0049327 | A1 | 2/2010 | Isch |
| 2010/0161065 | A1 | 6/2010 | Williams et al. |
| 2011/0035013 | A1* | 2/2011 | Winslow et al. ........... 623/19.13 |
| 2011/0106267 | A1* | 5/2011 | Grant ..................... 623/19.14 |

FOREIGN PATENT DOCUMENTS

| | | |
|---|---|---|
| EP | 103246 A1 | 3/1984 |
| EP | 329854 A1 | 8/1989 |
| EP | 339530 A2 | 11/1989 |
| EP | 339530 A3 | 3/1990 |
| EP | 329854 B1 | 11/1992 |
| EP | 538895 A2 | 4/1993 |
| EP | 538895 A3 | 6/1993 |
| EP | 581667 A1 | 2/1994 |
| EP | 776636 A1 | 6/1997 |
| EP | 903127 A2 | 3/1999 |
| EP | 1013246 A1 | 6/2000 |
| EP | 776636 B1 | 9/2000 |
| EP | 1064890 A1 | 1/2001 |
| EP | 1013246 B1 | 10/2003 |
| EP | 903127 A3 | 11/2003 |
| EP | 1402853 A2 | 3/2004 |
| EP | 1064890 B1 | 9/2005 |
| EP | 1402853 A3 | 3/2006 |
| EP | 1639966 A1 | 3/2006 |
| EP | 1639967 A1 | 3/2006 |
| EP | 903127 B1 | 6/2007 |
| EP | 1639966 B1 | 9/2007 |
| EP | 1902689 A1 | 3/2008 |
| EP | 1639967 B1 | 7/2008 |
| EP | 1402853 B1 | 5/2010 |
| EP | 1902689 B1 | 11/2011 |
| FR | 1064890 A | 5/1954 |
| FR | 2578162 A1 | 9/1986 |
| FR | 2579454 A1 | 10/1986 |
| FR | 2652498 A1 | 4/1991 |
| FR | 2683142 A1 | 5/1993 |
| FR | 2695313 A1 | 3/1994 |
| FR | 2704747 A1 | 11/1994 |
| FR | 2755847 A1 | 5/1998 |
| FR | 2776506 A1 | 10/1999 |
| FR | 2825263 A1 | 12/2002 |
| GB | 2297257 A | 7/1996 |
| WO | WO 0134040 A1 | 5/2001 |
| WO | WO 02067821 A2 | 9/2002 |
| WO | WO 03005933 A2 | 1/2003 |
| WO | WO 03030770 A2 | 4/2003 |
| WO | WO 02067821 A3 | 8/2003 |
| WO | WO 03005933 A3 | 10/2003 |
| WO | WO 03030770 A8 | 10/2003 |
| WO | WO 2007096741 A2 | 8/2007 |
| WO | WO 2007096741 A3 | 12/2007 |
| WO | WO 2011098890 A1 | 8/2011 |

OTHER PUBLICATIONS

Translation of FEP0339530—Inventor: Hans Grundel: Date of Publ. Nov. 2, 1989.
Print Out From Espacenet of FR2704747A1—Inventor Didier Capon, et al: Date of Publ Nov. 10, 1994.
Print Out From Espacenet of FR2776505(A1)—Inventor Katz Denis et al, Date of Publ Oct. 1, 1999.
EPO SR for DEP6138 (EP09178360) Dated May 12, 2010 (7 Pages).
Biomet Biomodular Low Profile Modular Glenoid, Biomet Corporation, One Page, Available At Least As Early As Nov. 24, 2010.
Biomet Biangular Standard Metal Backed Glenoid, Biomet Corporation, One Page, 1996.
Kirschner Integrated Shoulder System for Hemi & Total Shoulder Arthroplasty, Kirschner Medical Corporation, Two Pages, Available At Least As Early As Nov. 24, 2010.
The Cofield Total Shoulder System, Smith & Nephew Richards, Inc., Two Pages, Available At Least As Early As Nov. 24, 2010.
European SR Completed Sep. 10, 1999, Mailed Sep. 17, 1999.
PCT Search Report for PCT/US2011/061347, Dated Feb. 9, 2012, 11 Pages.
PCT Search Report for PCT/US2011/061357, Dated Feb. 3, 2012, 18 Pages.

* cited by examiner

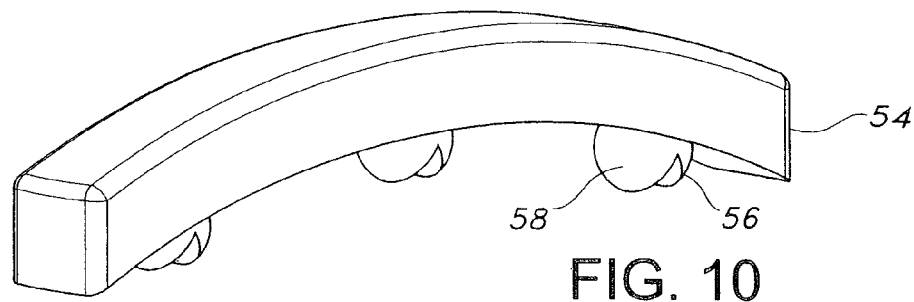
FIG. 10
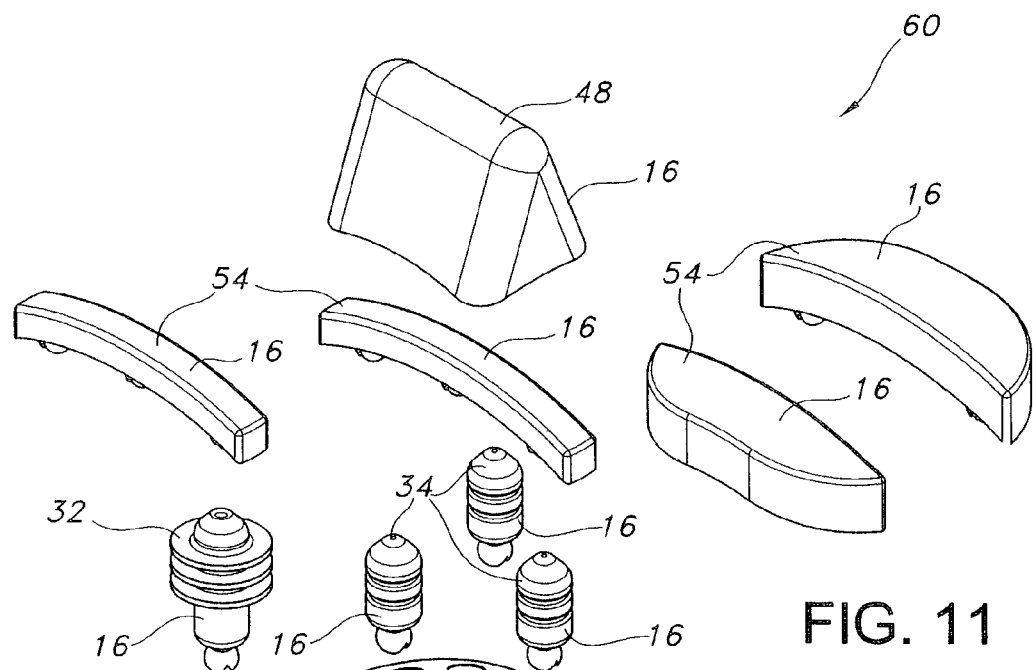
FIG. 11
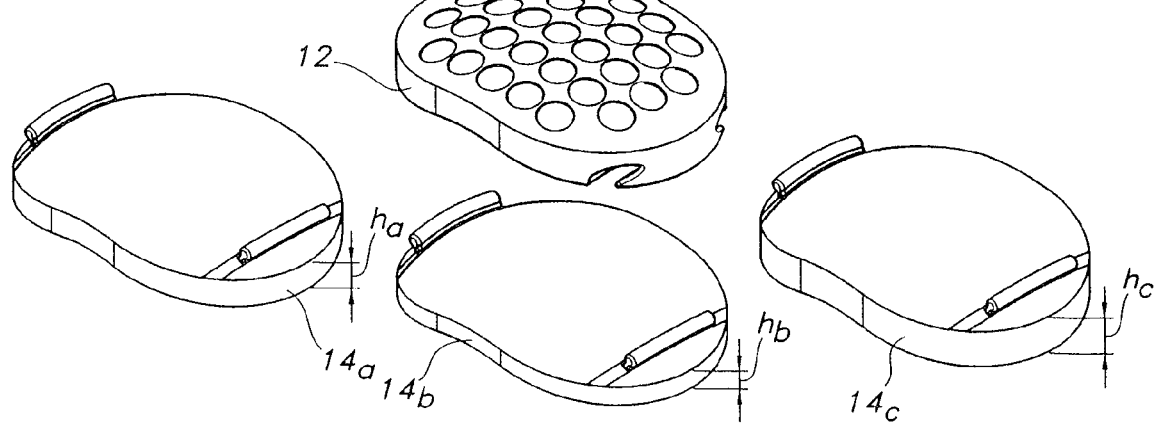

MODULAR GLENOID PROSTHESIS

CROSS-REFERENCE TO RELATED APPLICATION

Cross reference is made to the following application: DEP6346USNP entitled "MODULAR GLENOID PROSTHESIS" filed concurrently herewith, which is incorporated herein by reference.

TECHNICAL FIELD

The present invention relates to a prosthetic glenoid component and particularly to a modular glenoid assembly for attachment to a glenoid surface of a scapula to replace a natural socket of a shoulder and to provide a bearing surface for a head portion of an arm bone or humerus.

BACKGROUND

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component typically has an elongated intramedullary stem which is utilized to secure the humeral component to the patient's humerus. In such a total shoulder replacement procedure, the natural glenoid surface of the scapula is resurfaced or otherwise replaced with a glenoid component which provides a bearing surface for the head portion of the humeral component.

Glenoid components have heretofore been designed which include a number of plastic inserts coupled to metal backings. The metal backings are provided to secure the plastic inserts to the glenoid surface of the scapula. However, use of such two-piece glenoid components has a number of drawbacks associated therewith. For example, it is possible over the useful life of the glenoid component for the plastic inserts to separate from the metal backing thereby necessitating replacement of the glenoid component. In addition, over time wear of the plastic insert inherently occurs at the interface between plastic insert and the metal backing. It is possible for the plastic insert to wear to a degree which necessitates replacement of the glenoid component. It should be appreciated that in either case, such replacement of the glenoid component requires the patient to again be subjected to a surgical procedure and the subsequent recovery period associated therewith.

In response to the shortcomings associated with two-piece glenoid component designs, a number of one-piece glenoid components have heretofore been designed. In regard to such one-piece designs, a body portion, having a bearing surface defined therein for receiving the head of the humeral component, has a number of attachment pegs integrally formed therewith. The attachment pegs are advanced and thereafter secured into a corresponding number of holes which are drilled in the glenoid surface of the scapula by use of bone cement. An example of such a one-piece glenoid component that is designed to be secured to the scapula by use of bone cement is disclosed in U.S. Pat. No. 5,032,132 issued to Matsen, III et al.

As with the two-piece designs, certain one-piece glenoid components which have heretofore been designed have a number of drawbacks associated therewith. For example, some studies have speculated that it may be desirable to secure artificial components to natural bone structures without the use of bone cement. Glenoid components which have been designed to be secured to the scapula by the use of bone cement generally cannot be secured to the natural glenoid without use of the same.

Many glenoid component designs have been manufactured to address different types of scapular deficiencies. For example, some glenoid components have anchor pegs with flexible fins that are designed to act as barbs when inserted into the scapula. Other designs may utilize glenoid components with a buttress extending from the glenoid to fill larger defects in the natural glenoid. These may also include anchor and/or stabilizing pegs. In other embodiments a vault-filling glenoid may be used to fill a natural glenoid that has severe defects.

However, one problem with even existing modular designs, is that they do not provide the surgeon with the option of using different designs once surgery has started. Also, if a kit was to include all the different sizes and variations, the kit would be quite large and cumbersome to bring into surgery.

Another problem is that glenoid bone quality and surface deterioration varies significantly from patient-to-patient. Therefore, in current designs, having standard peg or buttress or vault locations may not work with specific patients' anatomy.

Another problem faced by surgeons during the procedure is that if the glenoid is partially eroded, ligament tensioning may be less than ideal. In some prior art designs, a stepped glenoid is provided to allow the surgeon to fill the eroded glenoid. However, these glenoids come in predetermined sizes and the size of the step (height and width) may not appropriately fill the glenoid erosion.

SUMMARY

According to one embodiment of the present invention, a modular glenoid assembly is provided. The modular glenoid includes a base having a first side and an opposing second side. The first side includes a plurality of connection features arranged in an array. The modular glenoid also includes at least one glenoid attachment member, the glenoid attachment member having a locking mechanism sized and shaped to lock the glenoid attachment member in at least one of the plurality of connection features on the base.

According to another embodiment of the present invention, a kit for use in a shoulder arthroplasty is provided. The kit includes a modular glenoid assembly. The modular glenoid assembly includes a base having a first side and an opposing side. The first side includes a plurality of connection features arranged in an array. The modular glenoid assembly further including a glenoid attachment member selected from a plurality of glenoid attachment members. Each of the plurality of glenoid attachment members have a locking mechanism sized and shaped to connect the base with the glenoid attachment member. At least one of the plurality of glenoid attachment members has a shape different than at least one other of the plurality of glenoid attachment members and wherein the locking mechanism of each of the plurality of glenoid attachment members is the same.

According to yet another embodiment of the present invention, a method for assembling a glenoid assembly is provided. The method includes using a base having a first side and an opposing second side. The first side includes a plurality of connection features arranged in an array. The method further includes using a plurality of glenoid attachment members, each of the plurality of glenoid attachment members having a locking mechanism. One of the plurality of glenoid attachment members is selected. The base is connected to the selected one of the plurality of glenoid attachment members by connecting the locking mechanism of the selected one of the plurality of glenoid attachment members to one of the plurality of connection features of the base.

BRIEF DESCRIPTION OF THE DRAWINGS

FIG. 10 is a perspective view of an augment according to the glenoid assembly of FIG. 8 or 9.

FIG. 11 is an illustration showing a kit for making a modular glenoid assembly according to one embodiment of the present invention.

Additional features of the present invention will become apparent to those skilled in the art upon consideration of the following detailed description of preferred embodiments exemplifying the best mode of carrying out the invention as presently perceived.

DETAILED DESCRIPTION OF THE DRAWINGS

Figure 1:
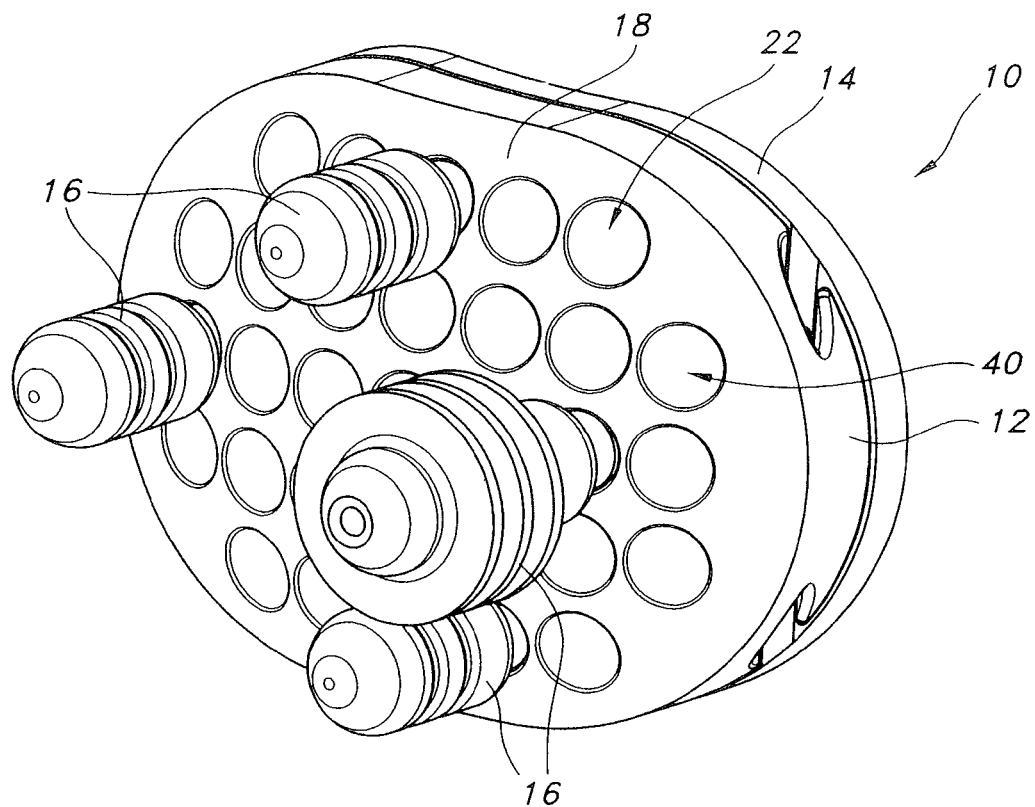
FIG. 1 is a perspective view of a glenoid assembly according to one embodiment of the present invention.
Figure 2:
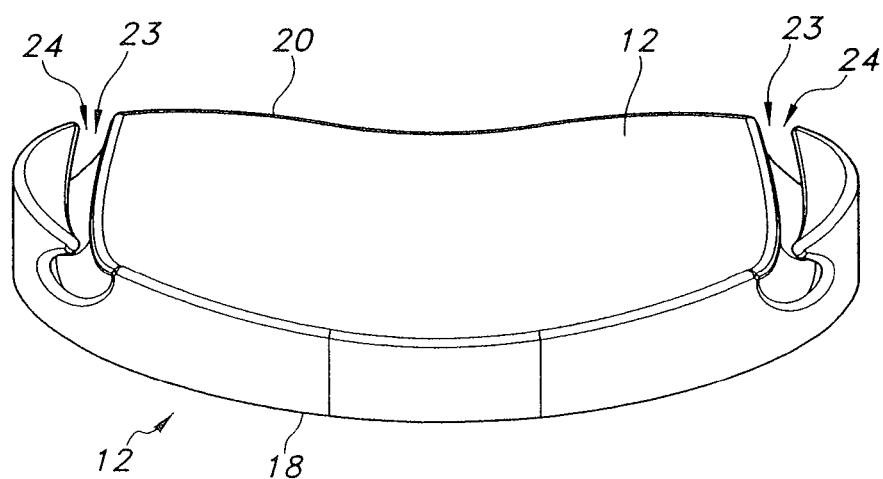
FIG. 2 is a side view of a base of the glenoid assembly of FIG. 1.

A modular glenoid assembly 10 is provided in accordance with the present invention. FIG. 1 shows glenoid assembly 10 including a base 12, an offset 14, and a glenoid attachment member 16. As shown in FIGS. 1 and 2, the base 12 includes a first side 18 and a second side 20. The first side includes a plurality of connection features 22 arranged in an array. The second side 20 of the base 12 includes a locking feature 23. In this embodiment, the locking feature 23 is a pair of receptacles 24.

Figure 3:
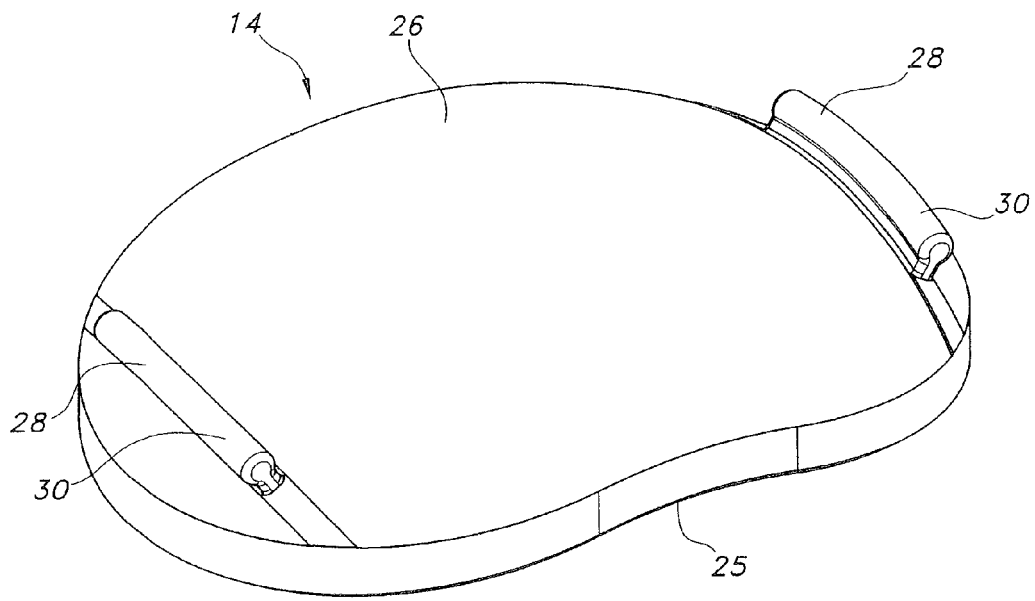
FIG. 3 is a perspective view of an offset of the glenoid assembly of FIG. 1.

Turning now to FIG. 3, the offset 14 is illustrated. The offset includes an articulation side 25 an opposing coupling side 26. The articulation side 24 is sized and shaped to articulate with a humeral component (discussed further below with respect to FIG. 5). The opposing coupling side 26 includes a locking feature 28. In this embodiment, the locking feature 28 is a pair of protrusions 30 that lock into the receptacles 22 of the base 12. In other embodiments, other known locking features may be used, such as dovetails, and snap locks.

Figures 4A, 4B:
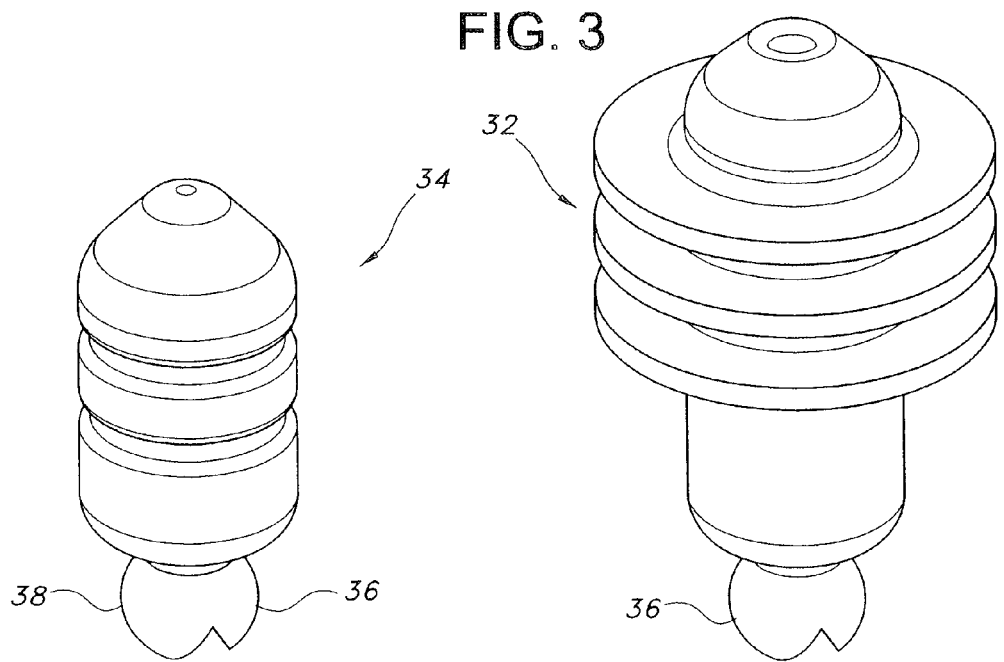
FIG. 4a is a side view of a cemented peg of the glenoid assembly of FIG. 1.
FIG. 4b is a side view of an anchor peg of the glenoid assembly of FIG. 1.

Referring now to FIG. 4, a plurality of glenoid attachment members 16 are shown. In this embodiment, the glenoid attachment member 16 includes a finned anchor peg 32 and a plurality of cemented pegs 34. Each of the glenoid attachment members 16 include a locking mechanism 36 sized and shaped to lock the glenoid attachment member 16 into at least one of the plurality of connection features 22 on the base 12. In the embodiment illustrated in FIGS. 1 and 4, each of the finned anchor peg 32 and cemented pegs 34 have a locking mechanism 36.

In this embodiment, the locking mechanism 36 is a ball-shaped member 38 and the connection features 22 are each generally spherical shaped receptacles 40 that are sized and shaped to lock the ball shaped member 38 into place. As described above, the generally spherical shaped receptacles are arranged in an array. In this embodiment, each of the connection features is the same size, allowing for the user to place the glenoid attachment members 16 anywhere along the array. Giving the user this flexibility allows the user to select the best location for the attachment members 16 based upon bone stock or other considerations. Also, because the locking mechanism 36 and the connection features 22 are generally spherical (balls and receptacles respectively) the user may insert the finned anchor peg 32 and/or cemented pegs 34 at a variety of different angles.

In other embodiments, the locking mechanism 36 may be of a different size, so long as it is able to lock into the connection feature 22. Furthermore, in other embodiments, the finned anchor pegs 32 and cemented pegs 34 may be of different sizes and shapes.

Figure 5:
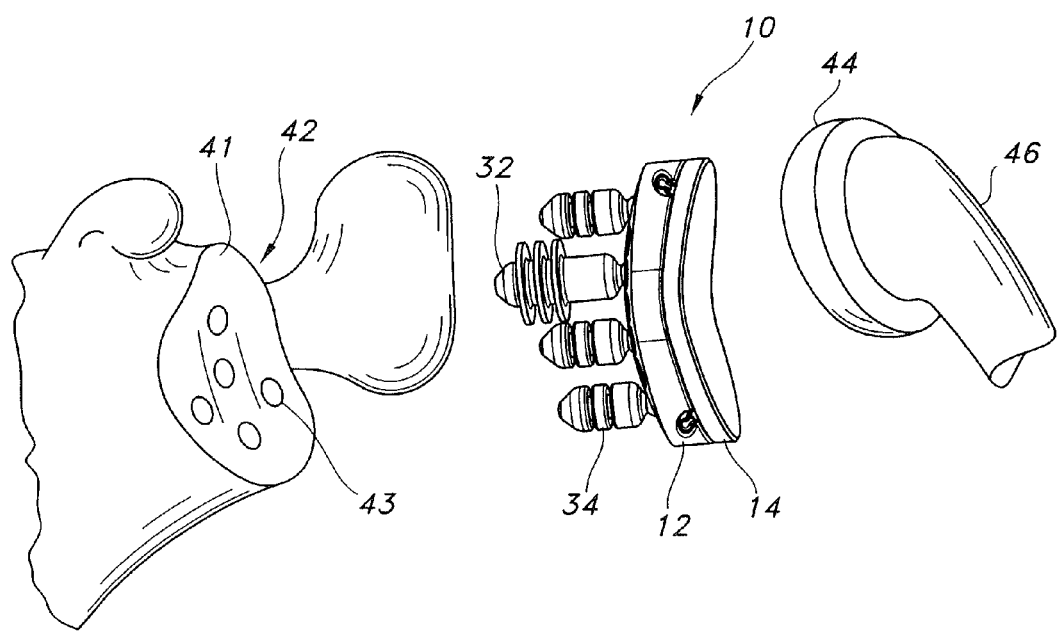
FIG. 5 is a perspective view of the modular glenoid assembly of FIG. 1 positioned between a glenoid surface of a scapula and a humeral component.

Turning now to FIG. 5, the glenoid assembly 10 is shown located between a glenoid surface 41 of a scapula 42 and a head portion 44 of a humeral component 46. Glenoid assembly 10 is designed to be attached to glenoid surface 41 of scapula 42 to replace the natural glenoid surface. As shown, the finned anchor peg 32 and cemented pegs 34 correspond to holes 43 drilled into the glenoid surface 41. The finned anchor peg 32 and cemented pegs 34 will be placed in the holes 44, locking the glenoid assembly 10 to the glenoid surface 40.

The articulation side 24 of the offset 14 is smooth and will articulate with the head portion 44 of the humeral component 46. In some embodiments, the head portion 44 may also be an implant. In other embodiments, the head portion 44 may be the natural humeral head. Although this embodiment shows the offset 14, in some embodiments, the base 12 may not need to be coupled to an offset and the second side 18 of the base 12 may be used to articulate directly with the head portion 44 of the humeral component. In those embodiments, the base 12 may not include the locking feature 23 described above.

Figure 6:
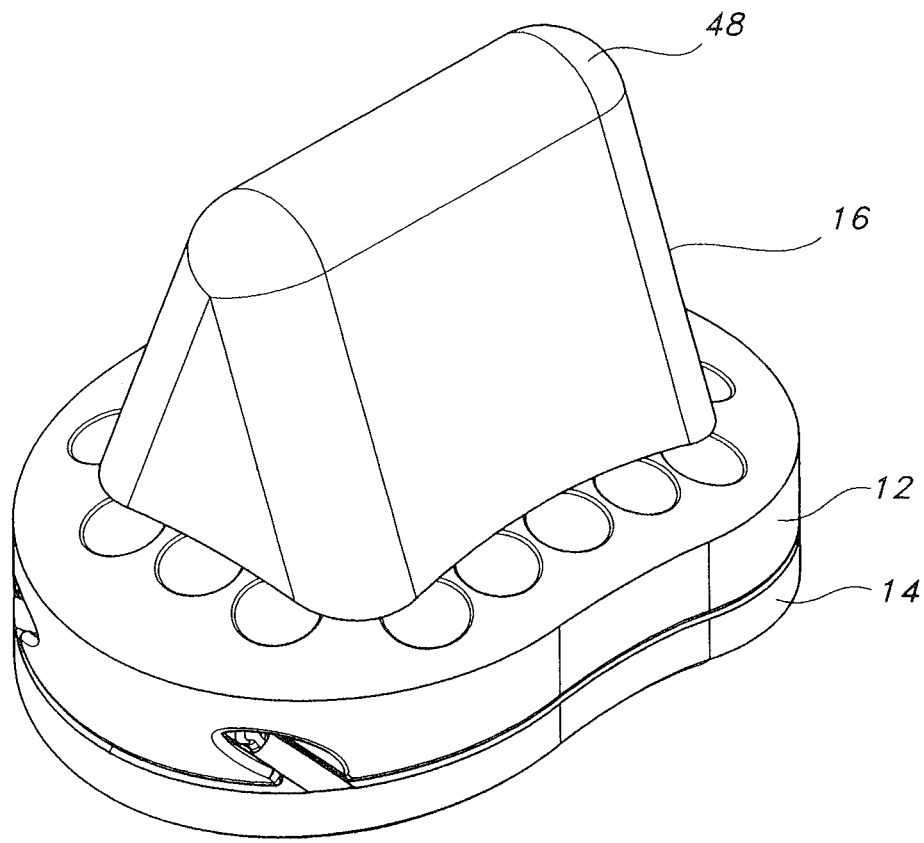
FIG. 6 is a perspective view of a glenoid assembly according to another embodiment of the present invention.
Figure 7:
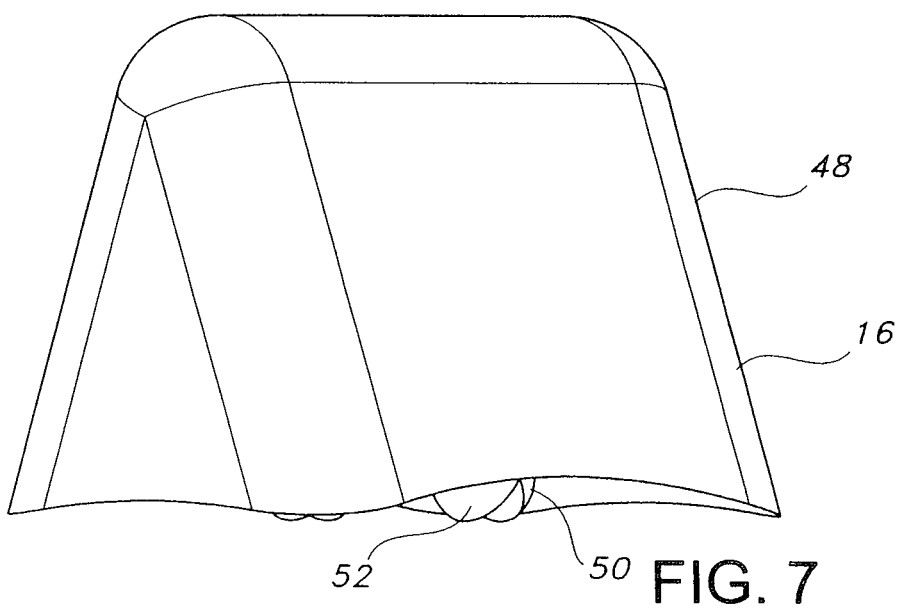
FIG. 7 is a perspective view of a wedge-shaped filler of the glenoid assembly of FIG. 6.

Turning now to FIGS. 6 and 7, the base 12 is illustrated coupled to the offset 14 and the glenoid attachment member 16. In this embodiment, the glenoid attachment member 16 is a wedge-shaped filler 48. The wedge-shaped filler is designed to fill a defect (not shown) in the glenoid 41 (FIG. 5) and to couple the base 12 and offset to the glenoid 41. The wedge-shaped fill 48 includes a locking mechanism 50. In the embodiment illustrated in FIGS. 6 and 7, the locking mechanism 50 is a ball-shaped member 52. The ball-shaped member 52 is the same size as the ball-shaped member 38 of the anchor peg 32 and cemented pegs 34. By utilizing the same dimensioned locking mechanisms 36, 50, both the wedge-shaped filler 48 and the pegs 32, 34 can be used with the same base 12.

Figure 8:
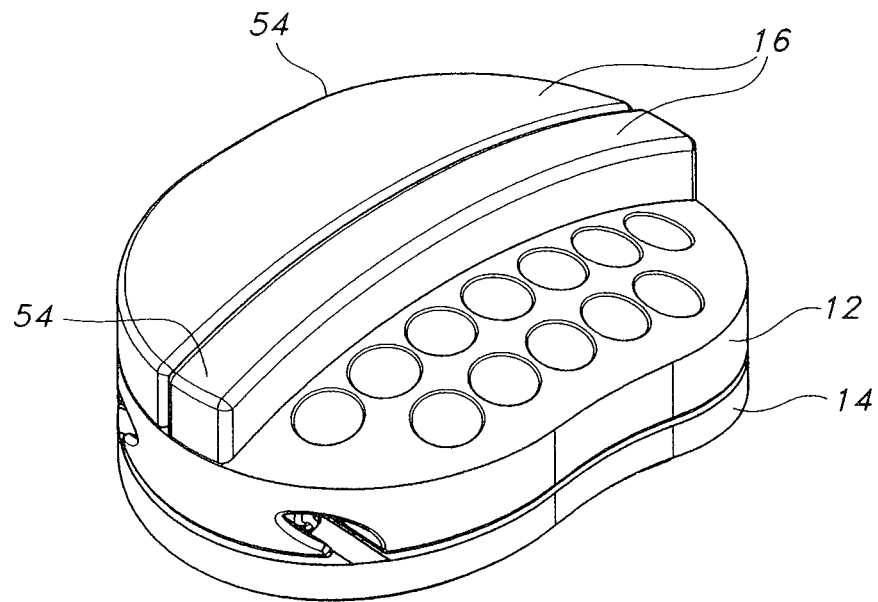
FIG. 8 is a perspective view of a glenoid assembly according to another embodiment of the present invention.
Figure 9:
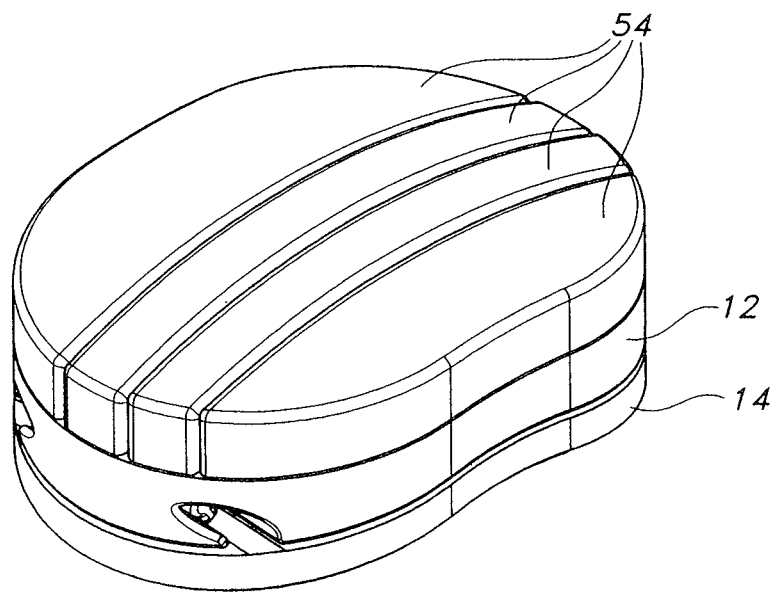
FIG. 9 is a perspective view of another glenoid assembly according to another embodiment of the present invention.

Another component of the present invention is illustrated in FIGS. 8-10. In this embodiment, the base 12 is coupled to an offset and a plurality of glenoid attachment members 16. In this embodiment, the glenoid attachment members 16 are augments 54. The augments 54 are designed to fill defects in the glenoid 41. The augments 54 may be of different heights, allowing the surgeon to fill different sizes of defects within the glenoid. Each of the augments 54 includes a locking mechanism 56 designed to fit within the connection feature 22 of the base 12. In the illustrated embodiment, the locking mechanism 56 of each of the augments 54 is a ball-shaped member 58 that fits into the generally spherical recesses 40 of the base 12. As stated above, by having the ball-shaped member 58 be of the same size as the ball-shaped members 38, 52 of the pegs 32, 34, and wedge-shaped filler 48 allows the user to use a single base 12 with multiple components, depending upon the needs of the patient.

As shown in FIG. 8, two differently sized augments 54 are coupled to the base. Alternatively, the user could select more augments 54 as shown in FIG. 9. FIGS. 8 and 9 are merely examples, any number of augments 54 may be used depending upon the defect to be corrected.

Turning now to FIG. 11, a kit 60 is illustrated. The kit 60 includes a base 12, a plurality of offsets 14a, 14b, 14c, and a plurality of glenoid attachment members 16a, 16b, 16c, 16d. As shown, each of the plurality of offsets 14a, 14b, 14c has a different height $h_a$, $h_b$, $h_c$. By offering offsets 14a, 14b, 14c of differing heights, the user can pick an offset to fit an individual patient's needs. The offsets 14a, 14b, 14c, allow the user (in this case a surgeon or other operating room personnel) to select an offset that will best restore ligament and/or tendon tension to the joint. The differing sizes of offsets allows the user to lateralize the humerus depending upon the patient. The user may choose to lateralize the humerus more in order to tighten the rotator cuff. Differing numbers of offsets 14 may be included.

The plurality of glenoid attachment members 16 include a plurality of cemented pegs 34, a finned anchor peg 32, a wedge-shaped filler 48, and a plurality of augments 54. In other embodiments, other numbers of each of the glenoid attachment members 16 may be included. Also, in some embodiments, some of the attachment members 16 may not be included. In other embodiments, there may be other glenoid attachment members 16 such as pins, screws, nails, un-finned anchor pegs.

The plurality of different types of glenoid attachment members 16 allows the user (such as a surgeon) to select the type of glenoid attachment member 16 that bests suits the individual patient. For example, if the patient's glenoid is relatively healthy, the surgeon may use only the finned anchor peg 32 and one or more cemented pegs 34. If there is slightly worse wear, the surgeon may use one or more of the augments 54. In some embodiments, the augments 54 may be used in conjunction with anchor pegs 32 and/or cemented pegs 34. Any number and combination of augments 54 may be used to best fit the patient's needs. In cases where the patient has experience sever wear and deterioration of the glenoid, the wedge-shaped filler 48 may be used.

One advantage of the kit 60 as illustrated other than the ability to mix and match is that each of the glenoid attachment members 16 has the same locking mechanism and that the connection features 22 are all sized and shaped the same. This allows the user to place the attachment members 16 into any of the connection features 22, depending on the patient's anatomy.

In the illustrated embodiment, the base 12, offsets 14, and glenoid attachment members 16 are all made of ultra-high molecular weight polyethylene. In other embodiments, the base 12, offsets 14, and glenoid attachment members may be manufactured using biocompatible metals or other biocompatible plastics. Alternatively, it is also contemplated that the base 12, offsets 14, and glenoid attachment members 16 may not all be manufactured using the same materials.

Figure 12:
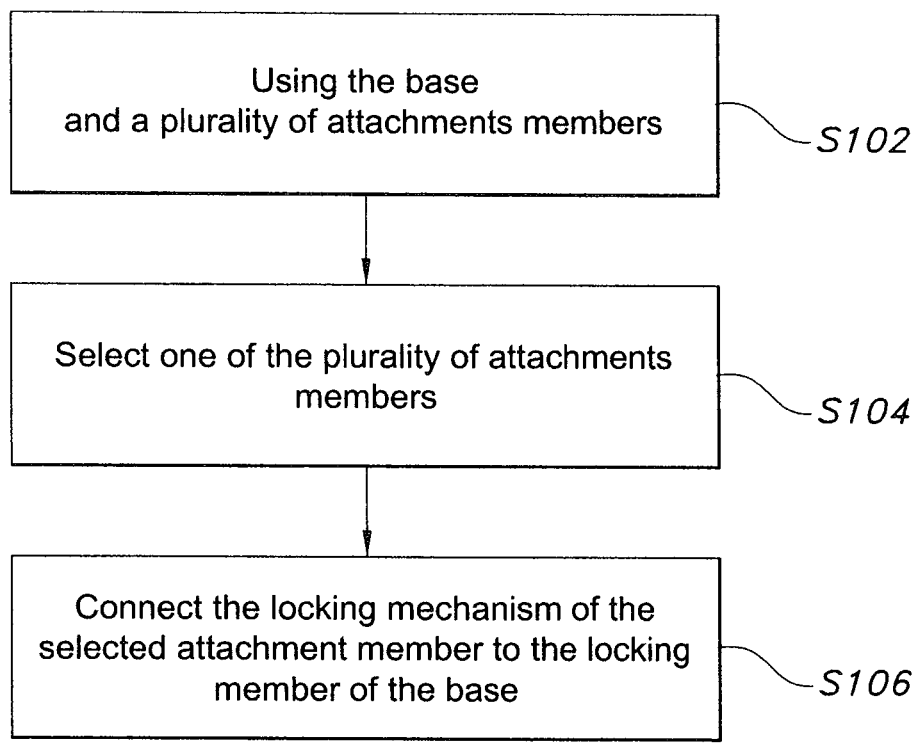
FIG. 12 is a flow chart illustrating a method for assembling the modular glenoid assembly according to one embodiment of the present invention.

Turning now to FIG. 12, a flow chart illustrating a method according to one embodiment is illustrated. At step s102, the method includes using the base 12 and a plurality of attachment members 16. The base 12 has a first side 18 and an opposing second side 20. The second side 20 includes a plurality of connection features 22. Each of the plurality of attachment members 16 includes a locking mechanism 36. At step s104, one of the plurality of glenoid attachment members 16 is selected. The base 12 is then connected to the selected one of the plurality of glenoid attachment members 16 by connecting the locking mechanism 36 of the selected one of the plurality of glenoid attachment members 16 to one of the plurality of connection features 22 of the base 12 (step s106). As described above, the plurality of glenoid attachment members 16 may include finned anchor pegs 32, cemented pegs 34, wedge-shaped fillers 48, and augments 54 and the locking mechanism 36 of each of the plurality of glenoid attachment members 16 is the same, so that any of the glenoid attachment features 16 may be locked into the base 12.

In some embodiments, the user may decide to insert the selected attachment member 16 first into the drilled glenoid 41. Next, the user will then lock the base 12 onto the selected attachment member 16. In other embodiments, the user may pre-assemble the base 12 and the selected attachment member 16 prior to inserting the implant 10 into the glenoid 41.

In some embodiments, the method may further include using a plurality of offsets 14 and selecting one of the plurality of offsets 14. The selected offset 14 is then connected to the base 12 as described above in reference to FIGS. 1-5.

Although the invention has been described in detail with reference to a preferred embodiment, variations and modifications exist within the scope and spirit of the invention as described and defined in the following claims.

The invention claimed is:

1. A modular glenoid assembly, comprising:
a base having a first side and an opposing second side, the first side including a plurality of connection features arranged in an array; and
at least one glenoid attachment member, the glenoid attachment member having a locking mechanism sized and shaped to lock the glenoid attachment member in at least one of the plurality of connection features on the base, wherein the plurality of connection features are a plurality of generally spherical-shaped recesses and the at least one glenoid attachment member is a wedge-shaped filler, and the locking mechanism of the wedge-shaped filler is a plurality of ball-shaped members, each of the plurality of ball-shaped members locking into the spherical-shaped recesses.

2. The modular glenoid assembly of claim 1, further comprising an offset, the offset having an articulation side sized and shaped to articulate with a humeral component and an opposing coupling side, the opposing coupling side having a locking feature, wherein the base includes a locking feature on the opposing second side, the base locking feature sized and shaped to connect to the coupling side locking feature.

3. The modular glenoid assembly of claim 2, wherein the opposing coupling side locking feature includes a pair of protrusions and the base locking feature includes a pair of receptacles sized and shaped to engage the pair of protrusions on the opposing coupling side locking feature.

4. The modular glenoid assembly of claim 2, further comprising a plurality of offsets, each of the plurality of offsets having a height, wherein the height of one of the plurality of offsets differs from the height of at least one of the other offsets.

5. The modular glenoid assembly of claim 1, wherein the at least one glenoid attachment member is a plurality of glenoid attachment members.

6. The modular glenoid assembly of claim 1, wherein the locking mechanism of the at least one glenoid attachment member is a ball-shaped member and the plurality of connection features are generally spherical shaped receptacles sized and shaped to lock the ball-shaped member of the at least one glenoid attachment member into place.

7. The kit of claim 1, wherein plurality of glenoid attachment members includes a plurality of augments, wherein the size and shape of one of the plurality of augments differs from the size and shape of at least one other of the plurality of augments.

8. A kit for use in a shoulder arthroplasty, comprising:
a modular glenoid assembly including
a base having a first side and an opposing side, the first side including a plurality of connection features arranged in an array, and
a glenoid attachment member selected from a plurality of glenoid attachment members, each of the plurality of glenoid attachment members having a locking mechanism sized and shaped to connect the base with the glenoid attachment member, wherein at least one of the plurality of glenoid attachment members has a shape different than at least one other of the plurality of glenoid attachment members and wherein the locking mechanism of each of the plurality of glenoid attachment members is the same, wherein the plurality of glenoid attachment member is comprised of an anchor peg, a cemented peg, a wedge-shaped filler, and an augment.

9. The kit of claim 8, further comprising a
a plurality of offsets, each of the plurality of offsets having an articulation side sized and shaped to articulate with a humeral component and an opposing coupling side, the opposing coupling side having a locking feature, wherein the base includes a locking feature on the opposing second side, the base locking feature sized and shaped to connect to the coupling side locking feature.

10. The kit of claim 9, wherein each of the plurality of offsets has a height, and the height of at least one of the plurality of offsets differs from the height of another of the plurality of offsets.

11. The kit of claim 9, wherein the base locking feature includes a pair of recesses and the coupling side locking feature includes a pair of protrusions sized and shaped to fit into the recesses.

12. The kit of claim 11, wherein the recesses are curved recesses and the protrusions are flexible curved protrusions that snap-lock into the recesses.

13. The kit of claim 9, further comprising:
a stem sized and shaped to fit into a humeral canal; and
a humeral head having a coupling feature adapted to couple with the stem and an articulation portion sized and shaped to articulate against the articulation side of one of the plurality of offsets.

* * * * *